United States Patent
Radomyshelsky et al.

(10) Patent No.: US 9,176,068 B1
(45) Date of Patent: Nov. 3, 2015

(54) UTILITY ELECTRONIC PRECIOUS GEMSTONE TYPE AND QUALITY DETECTOR

(71) Applicants: Leonid Radomyshelsky, San Diego, CA (US); Boris Loginov, San Diego, CA (US)

(72) Inventors: Leonid Radomyshelsky, San Diego, CA (US); Boris Loginov, San Diego, CA (US)

(*) Notice: Subject to any disclaimer, the term of this patent is extended or adjusted under 35 U.S.C. 154(b) by 0 days.

(21) Appl. No.: 14/551,047

(22) Filed: Nov. 23, 2014

(51) Int. Cl.
*G01N 21/64* (2006.01)
*G01N 21/87* (2006.01)
*G01J 1/58* (2006.01)

(52) U.S. Cl.
CPC . *G01N 21/87* (2013.01); *G01J 1/58* (2013.01); *G01N 21/6402* (2013.01); *G01N 21/645* (2013.01); *G01N 2021/6417* (2013.01); *G01N 2201/0612* (2013.01)

(58) Field of Classification Search
CPC .................................. G01J 1/58; G01N 21/645
See application file for complete search history.

(56) References Cited

U.S. PATENT DOCUMENTS

| | | | |
|---|---|---|---|
| 5,118,181 A | 6/1992 | Yifrach | |
| 5,206,699 A | 4/1993 | Stewart | |
| 5,835,205 A * | 11/1998 | Hunter et al. | 356/30 |
| 6,043,742 A * | 3/2000 | Austin | 340/540 |
| 6,239,867 B1 | 5/2001 | Aggarwal | |
| 6,980,283 B1 * | 12/2005 | Aggarwal | 356/30 |
| 7,102,742 B2 | 9/2006 | Geurts | |
| 2011/0158057 A1* | 6/2011 | Brewer et al. | 368/239 |
| 2011/0292376 A1* | 12/2011 | Kukushkin et al. | 356/73 |
| 2013/0153515 A1* | 6/2013 | Kang et al. | 210/748.14 |

FOREIGN PATENT DOCUMENTS

CN   102699362 A  * 10/2012

* cited by examiner

*Primary Examiner* — Kiho Kim
(74) *Attorney, Agent, or Firm* — Selwyn S. Berg

(57) ABSTRACT

The Utility Electronic Precious Gemstone Type And Quality Detector (Utility Gem Tester) is a simple, portable, rugged and dependable hand held device that identifies gemstones and rates a gemstone's quality using an internal tabulation of the gemstone's wide spectral response to ultra violet irradiation. The device contains a low power UV LED and a multi-channel photodiode array for a wide band spectral analysis of a gemstone's response to the impinging UV laser beam. The spectral analysis is then compared with the internal tabulation of spectral fingerprints of known gemstones and an analysis is visually displayed. The Utility Gem Tester is intended to fill the needs of amateur (gemstone) rock hunters and jewelry kiosk personnel in identifying the various marketable precious stones.

13 Claims, 4 Drawing Sheets

Utility Gem Tester Assembly. Vertical cross section of the Gem Tester components within the testing stand FIGURE 1. Theoretical Principles of the Utility Gem Tester Ultra-violet solid state laser collimated beam illuminating a gemstone which emits broad spectral luminescence to an array of solid state detectors capable of electronically responding to the spectral content from visible to infra-red.

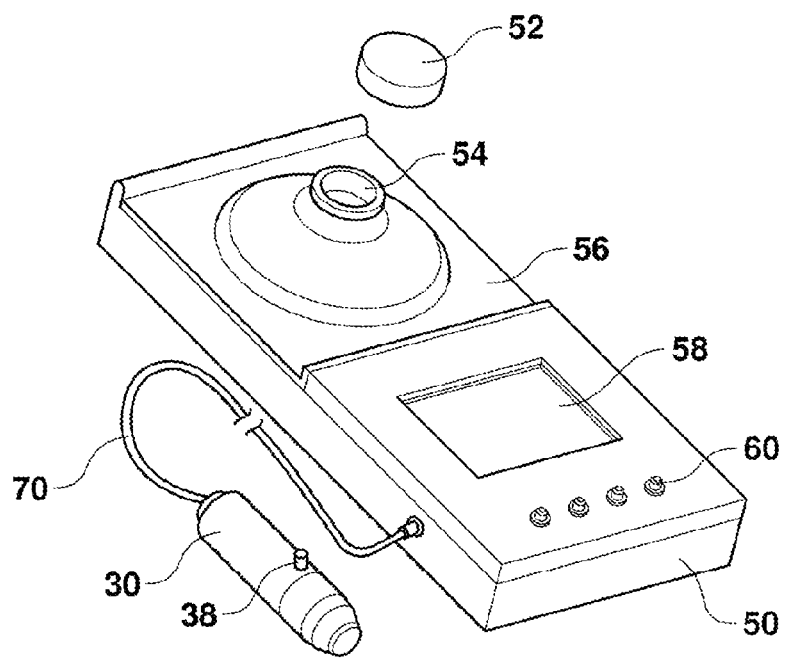
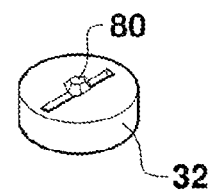
FIGURE 2 Utility Gem Tester. The assembly in external perspective and its various components.

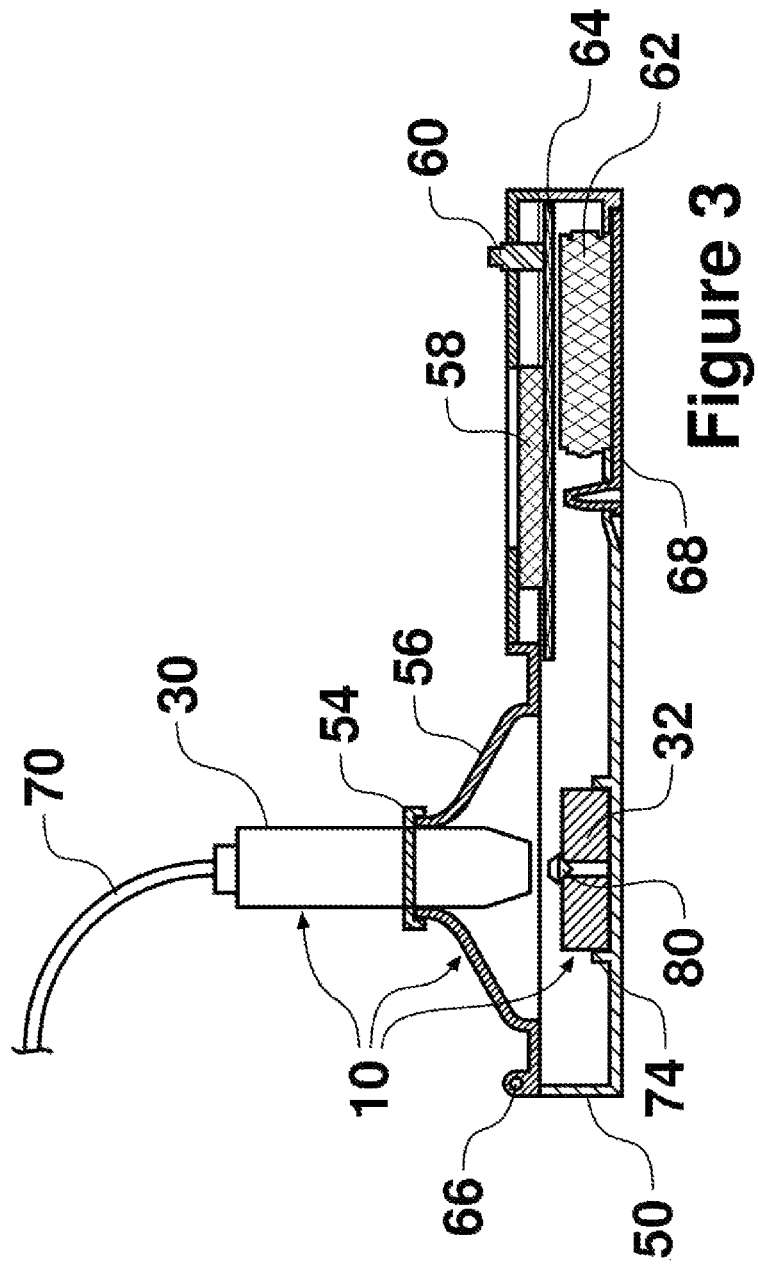
FIGURE 3 Utility Gem Tester Assembly. Vertical cross section of the Gem Tester components within the testing stand

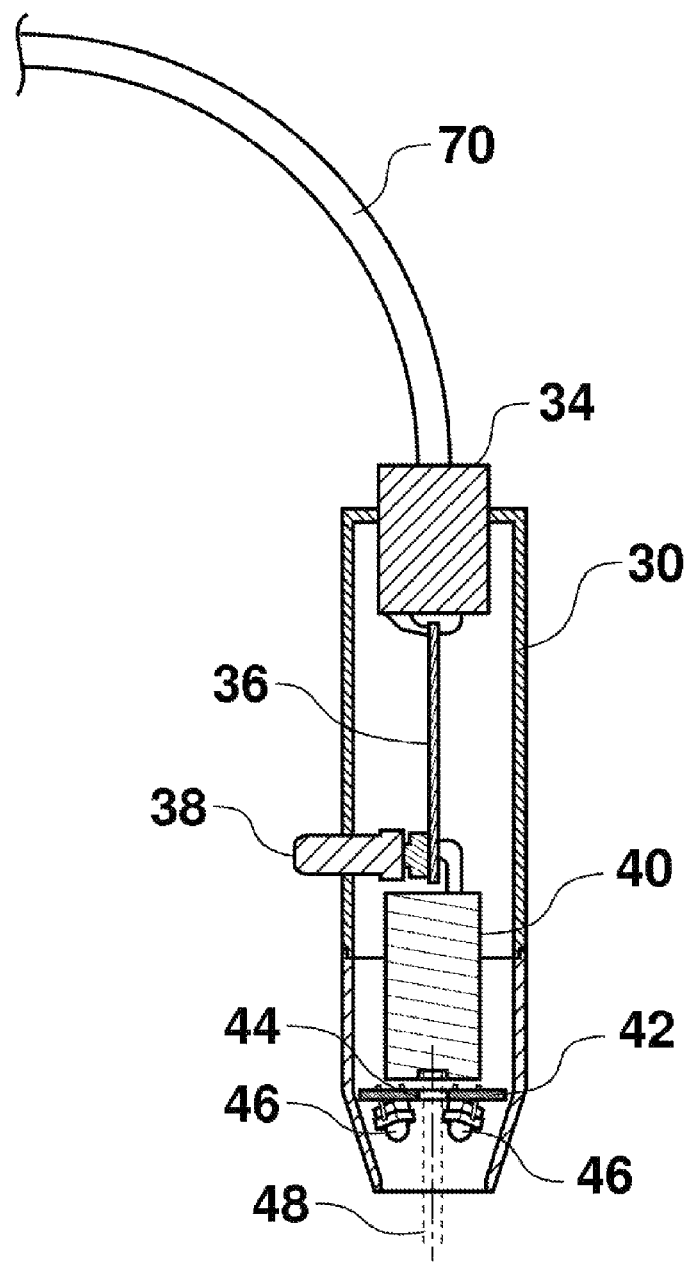
FIGURE 4 Probe Cross Section. The simple geometry of solid state UV LED laser and broad spectrum photo-diode detectors.

UTILITY ELECTRONIC PRECIOUS GEMSTONE TYPE AND QUALITY DETECTOR

CROSS-REFERENCE TO RELATED APPLICATIONS CITED

U.S. Patent Documents

Hunter, C. E. Waltz, D. G. (Feb. 10, 1997) U.S. Pat. No. 5,835,205 "OPTICAL TESTING SYSTEM FOR DISTINGUISHING A SILICON CARBIDE GEMSTONE FROM A DIAMOND"

Aggarwal, L. K. (May 29, 2001) U.S. Pat. No. 6,239,867 B1"APPARATUS AND METHOD FOR GRADING, TESTING AND IDENTIFINYING GEMSTONES"

Geurts, R. (Sep. 5, 2006) U.S. Pat. No. 7,102,742 B2"FLUORESCENCE MEASURING DEVICE FOR GEMSTONES"

Yifrach, A & Neta, U (Jun. 2, 1992) U.S. Pat. No. 5,118,181"METHOD AND APPARATUS FOR IDENTIFYING GEMSTONES PARTICULARLY DIAMONDS"

Stewart, A. D. J. et alia (Apr. 27, 1993) U.S. Pat. No. 5,206,699"SENSING A NARROW FREQUENCY BAND OF RADIATION AND GEMSTONES",

Reference Article

Zare, R. N (July 2012) Annual Review of Analytical Chemistry, Vol. 5: pp 1-14 "MY LIFE WITH LIF: A PERSONAL ACCOUNT OF DEVELOPING LASER-INDUCED FLUORESCENCE"

http://www.nobelprize.org/nobel_prizes/physics/laureates/2014/advanced-physicsprize2014_2.pdf "EFFICIENT BLUE LIGHT-EMITTING DIODES LEADING TO BRIGHT AND ENERGY-SAVING WHITE LIGHT SOURCES

FIELD OF THE INVENTION

This Utility Gem Tester invention is a simple compact device that accomplishes the identification and quality of precious stones and, in particular distinguishes natural gems such as ruby, emerald, sapphire, and others from their lab grown, processed, or counterfeited versions. The Proposed International Fields of invention are G01N 21/00, G01N21/64 which corresponds to U.S. 365/30, 365/425, 259/461.1

BACKGROUND OF THE INVENTION

Introduction

Gemstone identification is an art that has a history that spans over a thousand years. The primary system remains the direct visual tests of color and clarity. The visual approach resulted in the initial classification of the various precious stones such as diamonds, rubies, sapphires, etc. This may be augmented by the use of a microscope to check for inclusions as a determination of purity. There is also a supplementary test of looking for color changes which is defined as the difference between what you see in natural light versus incandescent lighting as a determination of quality. According to the present state of the art, gemstones are discerned from one another on the basis of differences relating to one or several physical characteristics such as optical transmission, thermal conductivity, electrical conductivity or specific gravity. There are now many more sophisticated tests that depend on refractive index utilizing the full spectrum of incident radiation from x-rays to masers and even electromagnetic responses. The use of many of these approaches requires analytical experience and expertise and sophisticated instrumentation. The technical challenge that currently exists is in the development of a dependable and rugged analytical device that gives a credible identification of a gem that can be used by the general public; i.e.,—a simple commercial instrument. Such a device can fill the widespread need by the various worldwide lapidary clubs of amateur gemologists who often take to the field as freelancers or collect and speculate in various gemstones of varying quality. Another marketing source is in the widespread jewelry businesses often located in kiosks in shopping malls, fairs or discount store counters and pawn shops. A simple gemstone identification and quality confirmation could increase consumer confidence considerably. Hence, there is a widespread need for a simple, dependable and rugged handheld device to confirm sales claims and also be used in the field by amateur gemologists. The within Utility Gem Tester will fill that need in the marketplace.

The pioneering research on laser induced fluorescence (LIF) of Professor Zare ("My Life with LIF: A Personal Account of Developing Laser-Induced Fluorescence;" *Annual Review of Analytical Chemistry*, Vol. 5: pp 1-14, July 2012) has produced a uniform catalog of the phenomena that may be associated with glowing gemstones. Induced fluorescence is a spectroscopic method which may be used for studying structure of molecules and detection of selective species of the molecules in a crystalline or gem-like structure. The species to be examined is excited with light from a laser or a L(ight)E(mitting)D(iode). The wavelength is often selected to be the one at which the species has its largest cross section for photon interaction. The excited species will, after some time—usually in the order of few nanoseconds to microseconds, de-excite and emit light at a wavelength longer than the excitation wavelength. This fluorescent light may then be registered with optically filtered photodiodes. The registered intensity and duration of the induced emitted light will correspond to a particular gem and its quality.

However, there are other more classical effects that may also be present in the optical emission. There can also be a Stokes shift where the emitted fluorescent light has a longer wavelength and lower energy than the absorbed light which is due to energy loss between the time a photon is absorbed and when it is emitted. The causes and magnitude of Stokes shift can be complex and are dependent on the fluorophore and its environment. Gemstones have a distinctive fluorescence or may fluoresce differently under short-wave ultraviolet and are often associated with the presence of various minerals included in the gemstone. There exists a compendium of spectral colors associated with the different common minerals usually found in a species of gemstones.

Another effect is known as Raman scattering or inelastic scattering of monochromatic light, usually from a laser or LED operating in the near ultraviolet range. The laser light interacts with molecular vibrations, phonons or other excitations in the system, resulting in the energy and wavelength of the incident photons being shifted up or down. The shift in energy gives information about the vibrational orbital electron modes in the system which is related to the species of gemstones to be identified or quality rated. Infrared spectroscopy yields similar, but complementary, information.

The classical elastic Rayleigh scattering of the incident illumination must be filtered out or otherwise accounted for in the output from the collected light dispersed onto a detector.

There have been rapid developments in industrial, low cost solid state photo detectors such as photo-diodes and phototransistors that are capable of analyzing color spectrum from the visible to the infra-red. These have been available for a reasonable period of time and are employed in exacting color analysis and low-light photography. The missing link had been the development of wide spectral range solid state lasers (SSL) and light emitting diodes (LED). However, in 2014 the Noble Prize was awarded to several scientists who were participants in the pioneering work on extending the output spectral range of the SSL and LED throughout the visible blue down to the ultra violet. ("Efficient Blue Light-Emitting Diodes Leading To Bright And Energy-Saving White Light Sources"). Currently there exist many competitive sources for both wide band solid state photo-detectors and ultra violet laser diodes which are rugged, dependable and operate at low power.

As a consequence of the complexity of the near infra-red luminous output of any gemstone, a plethora of valid patents for a diversity of methods exist, only a few of apparent relevance to the within invention of a simple and rugged utility electronic precious gemstone type and quality detecting device are discussed below, though many more have been reviewed. In general, these listed claimed inventions pertain to complex industrial devices and not a simple handheld device intended for general public use.

RELATED PATENTS AND ARTICLE

A brief key article written by the renown Stanford professor, Dr. R. N Zare is "My Life with LIF: A Personal Account of Developing Laser-Induced Fluorescence", which was published in the Annual Review of Analytical Chemistry, Vol. 5: 1-14 (July 2012). Its abstract is the clearest statement of the discovered phenomena and states:

Laser-induced fluorescence (LIF) is a spectroscopic technique that involves the excitation of a molecular target by a beam of laser radiation followed by the detection of the subsequent emission of radiation from the target. LIF detection has several advantages over absorption spectroscopy. First, LIF has excellent detection sensitivity because a signal is observed against a dark background. Second, the emitted radiation can be collected at various angles with respect to the incoming laser beam, making it possible to obtain two- and three-dimensional images because the fluorescence is emitted in all directions. Third, by dispersing the fluorescence, it is also possible to learn about the transitions from the state excited to the various lower levels of the target species. Finally, because of the delay between the excitation and detection events, it is also possible to learn about what processes the excited target undergoes in the intervening time.

This fundamental research is at the heart of the many ubiquitous world-wide patents which operate on the principle of optical identification of precious stones.

An application of that study is at the heart of U.S. Pat. No. 6,239,867 B1 of May 29, 2001, titled "Apparatus And Method For Grading, Testing And Identifying Gemstones" by Lalit K. Aggarwal, though it gives no direct credit to Dr. Zare. This omnibus disclosure ostensibly requires a complex system of its claimed housed platform from a plurality of different angles to get a three dimensional profile of the gem's fluorescence. There is no question on either the effectiveness of this fully automated system or its cost as a consequence of its complexity. It is a self-contained LIF laboratory. By contrast, the within disclosed Utility Gem Tester utilizes a simple laser diode and inexpensive photo-diodes combined in a compact electronic system for identification of precious gemstone type and quality. The device is a handheld device that utilizes a simple laser diode and photo-sensing diodes. There has been a long-term need for such a Utility Gem Tester by the worldwide membership of the numerous Lapidary Clubs.

U.S. Pat. No. 7,102,742 B2, issued Sep. 5, 2006, describing a "Fluorescence Measuring Device For Gemstones" of inventor Ronald Geurts is specified to be uniquely used for diamond inspection. The invention is claimed to need a plurality of Light Emitting Devices and is subject to intensity control by the user. By contrast, the within disclosure does not allow the user to make any adjustments as the within described heuristically programmed device is factory set so that the interpreting algorithm is not invalidated by varying the tested gemstone's fluorescence intensity. Also, the Geurts invention is intended as an industrial device for professional use. By contrast, the within described Utility Gem Tester is a simple device intended for use by the general public.

An early 1992 patent (U.S. Pat. No. 5,118,181) for a "Method And Apparatus For Identifying Gemstones Particularly Diamonds" by Aharon Yifrach et alia does suggest the general use of gemstone luminescence by excitation for gemstone identification. However, it does claim utilizing selective spectral analysis as the handle for the identification. By contrast, the Utility Gem Tester has an heuristic electronic tabular association of the fluorescence of the gemstone to its identity and quality.

Another device intended to distinguish real cut diamonds from a silicon carbide gemstone diamond substitute is described in the 1997 Hunter U.S. Pat. No. 5,835,205 which specifically looks at the transmissivity of a specific band of light from a broad band UV output from a brilliant quartz halogen incandescent lamp that generates a spectrum of light including a discriminating passband of ultraviolet energy by the gemstone. This technique may be useful for the limited applications of distinguishing diamond transmissivity from silicon carbide transmissivity, but is not capable of a broad application to all gemstones. The limited life of this patent was probably because its intended market of jewelers already had less complex methods of distinguishing fake diamonds from real ones. Please also note that the Hunter invention is intended to test only cut gemstones and not field minerals.

Perhaps the most convoluted omnibus patent is that of Stewart et alia for "Sensing A Narrow Frequency Band Of Radiation And Gemstones", U.S. Pat. No. 5,206,699 of Apr. 27, 1993. This patent has 91 claims and extensive list of references. However, this invention claims underlying physical analysis based on Raman emission which is only a component contributing phenomena in the within handheld device. The Stewart invention does also utilize complex spectrum analysis instead of simple IR sensitive photo-sensors.

None of the reviewed patents or research articles recognized the application of the more recent development of solid state UV lasers and LEDs and photodiodes to the technology of precious stone identification and grading as a simple utility hand-held device. It was in 1992 Japanese inventor Shuji Nakamura invented the first efficient blue LED. Continued development resulted in the refinement and extension of the output spectral range into the ultra-violet and in 2014, Nakamura and several others received the Nobel Prize in Physics for their ground breaking research ("Efficient Blue Light-Emitting Diodes Leading To Bright And Energy-Saving White Light Sources") There has been many technical articles written on the rapidly developing field of solid state lasers coupled with industrial developments that recommend this technology to a multiple multitude of applications, but none to gemstone identification.

There is no question that this is a crowded art area of similar patent disclosures in respect to a diversified technology, but—for the most part—the issued patents are sophisticated technical analytical apparatuses. However, the within inventors have surveyed their targeted market and noted the need for the hereinafter described handheld simple and rugged gemstone testing device/Utility Gem Tester. The pertinent value of the above references is to its listing and cross-listing of open source technical information which is only an excerpt of all the information that has been reviewed.

BRIEF SUMMARY OF THE INVENTION

This Utility Gem Tester is a portable, battery powered device comprising a test assembly of a test probe, decoding housing box and gem receptacle. A single gemstone or a jewelry piece with such stone is placed upon a mating fixture, preferably in the ambient light controlled decoding housing box. In the following description, the CAPITAL LETTERED COMPONENTS are the descriptive lexicography of the disclosed Utility Gem Tester.

The Utility Gem Tester evaluates a GEMSTONE by measuring its fluorescence under direct low-power radiation from a commercially available UV LASER DIODE ASSEMBLY which is located in the TESTING PROBE. The measurement is done by a commercially available broad spectrum SOLID STATE PHOTO DETECTOR ARRAY also in the TESTING PROBE. Broad Spectrum as practiced herein means within the frequency range of visible to infrared of 790 THz to 300 GHz. This is currently commercially achievable with an array of 16 photodiode spectral channels which include at least one in the infrared. Current research is directed at increased spectral channels with greater resolution and broadened spectral range.

The electrical output of the SOLID STATE PHOTO DETECTOR ARRAY is fed into the TESTING STAND which has a micro controller unit (MCU) on a ROM TESTING CIRCUIT BOARD that decodes and correlates the SOLID STATE PHOTO DETECTOR ARRAY signal outputs with heuristic information so as to visually display the GEMSTONE information on the ALPHA-NUMERIC READOUT. The entire test assembly can be hand held or placed on a desk top. (As an alternative, the TESTING PROBE may be used in a darkened environment without the TESTING STAND.) The UV LASER DIODE ASSEMBLY is an ultra-violet radiation source located in the TESTING PROBE. Its LASER BEAM activates visible and infra-red fluorescent emission from the stone in reaction to the applied UV radiation which is monitored by the SOLID STATE PHOTO DETECTOR ARRAY. Signals from the SOLID STATE PHOTO DETECTOR ARRAY are processed, and compared against data tables in the processor memory of the ROM TESTING CIRCUIT BOARD, which compares heuristically obtained data for a number of popular gems to conclude whether the GEMSTONE is a natural one, had been heat treated, had been grown artificially, or is an imitation. The result is visually displayed by the ALPHA-NUMERIC READOUT digital read-outs on the TESTING STAND.

This Utility Gem Tester is a simple electronic device which has been field tested to show that it is a dependable precious gemstone type and quality detector that is rugged and relatively low cost device suitable for field use by amateur gemologists, up-front salespersons in jewelry stores and precious stone collectors/speculators. It is a non-destructive testing device which attributes its low cost to the commercially available components of solid state photo detectors and laser diodes.

In the best current practice of this invention, the UV LASER DIODE ASSEMBLY is a commercially available 405 nanometers, 1 milliwatt, 6 volt LED device and is acceptable for public distribution since it is characterized as radiating soft low-level ultra-violet which is turned on for a fraction of a second during testing. The divergence of the dot shaped output UV laser beam is less than 0.5 millirads which is well collimated. As a back-up safety system, the Utility Gem Tester has a programmed electronic protocol for confirming close contact with the gem being tested before the laser is activated. That safety/accuracy protocol requires that the SOLID STATE PHOTO DETECTOR ARRAY initially measure the ambient luminosity before the laser is excited. If the luminosity is above a certain level, it indicates that the testing device is, possibly, facing open space and a good optical contact has not been made with the gem under test. Consequently, the laser is not turned on. In such case, a notice is annunciated to the user that a good optical contact has not been made. The pretest information is also employed to correct for ambient light leakage to the multichannel matrix of photo detectors.

The SOLID STATE PHOTO DETECTOR ARRAY is commercially available photodiodes/phototransistors which have a broad spectral sensitivity into the infra-red spectrum. The commercially available SOLID STATE PHOTO DETECTOR ARRAY of digital color light sensors are designed to accurately derive broad spectral color chromaticity and intensity of a luminous object and provide a digital output with 16-bits of resolution. These commercially available devices include an array of filtered photodiodes, analog-to-digital converters and control functions on a single monolithic CMOS integrated circuit. In-package trim capability assures that the device-to-device and system-to-system tolerance can be minimized allowing very precise repeatability. In the current best practice, the selected commercial SOLID STATE PHOTO DETECTOR ARRAY has been tested as to its sensitivity to input radiation of ambient light sources as well as a general scan of the spectrum and filtered light. To assure uniformity, a QC program was instituted. From the extensive testing, multiple sources for obtaining such SOLID STATE PHOTO DETECTOR ARRAYs have been established.

The SOLID STATE PHOTO DETECTOR ARRAY described herein has been calibrated by heuristics associated with the geometry of the device, its supplied components and a large selection of GEMSTONES. Such standardizing routines have established laboratory procedure protocols. Extensive in-house research has been conducted with standardized test gems that indicate a heuristic table can be determined which reliably relates different classes of gems into its commercial value. From the heuristic sampling, the electronic algorithm in the memory section of the MCU of the ROM TESTING CIRCUIT BOARD is obtained to relate the gemstones to the quality decision. The utility electronic precious gemstone type and quality detector device electronics has adjustable biases that factory sets the final electronic sensitivities. The user may select his guess of the gemstone identity on the TEST BUTTON ARRAY, e.g., Ruby, Sapphire, Spinal, Alexandrite, Emerald, Garnet, Red, Green, Blue, Or Variable. The program in the memory section of the MCU on the ROM TESTING CIRCUIT BOARD contains measurement results for all these varieties and the programming displays the outcome on the ALPHA-NUMERIC READOUT as the gem name accompanied with 'GENUINE', 'CULTURED', or 'IMITATION'. Possible other test outcomes include 'TRY AGAIN' and 'NO SENSOR' to cover possible testing blunders or uniqueness. Ongoing research is developing a broader range of responses and inquiries.

The assembled Utility Gem Tester is a simple hand-held instrument. Physically, It consists of three parts: pocket size main unit, the probe, and gem receptacle. The main unit has a test chamber with a lid for conducting a test sealed from ambient light. In this case the gem receptacle is placed inside the chamber and the probe is installed in the well in the center of the chamber lid. The test can also be conducted outside the chamber. One method is having the gem receptacle with the gem under test on a desktop and the probe in hand. If the gem to be tested is too big or is mounted on a piece of jewelry which does not fit in the receptacle, the test can be done with the jewelry piece held in one hand and the probe in the other.

The TESTING PROBE is shaped like a pen with the LASER BEAM projection orifice in the front tip. Within the TESTING PROBE is located the UV LASER DIODE ASSEMBLY and SOLID STATE PHOTO DETECTOR ARRAY with its commercially packaged control electronics. On the side of the TESTING PROBE is a PROBE TEST BUTTON which initiates the electronics and algorithm to elect an analytical read-out. The device measures ambient light before the laser beam illuminates the gem and the fluorescence from the gem illuminates the photodiodes on the SOLID STATE PHOTO DETECTOR ARRAY. Too bright ambient could indicate that the tip is not positioned tightly against the gem under test, therefore test is aborted. Otherwise, the pretest information is a corrective offset to the test reading photo diode output.

DESCRIPTION OF THE DRAWINGS

For a more complete understanding of the features and advantages of the present invention_, refer to the detailed description of the invention along with the associated figures in which corresponding numerals in the different figures refer to corresponding parts and in which:

FIG. 2 Utility Gem Tester is shown as an assembly in external perspective and its various components.

FIG. 3 Utility Gem Tester Assembly is shown as a vertical cross section of the components within the testing stand FIG. 4 Probe Cross Section shows the simple geometry of solid state UV LED laser and broad spectrum photo-diode detectors.

DETAILED DESCRIPTION OF THE INVENTION AND DRAWINGS

Figure 1:
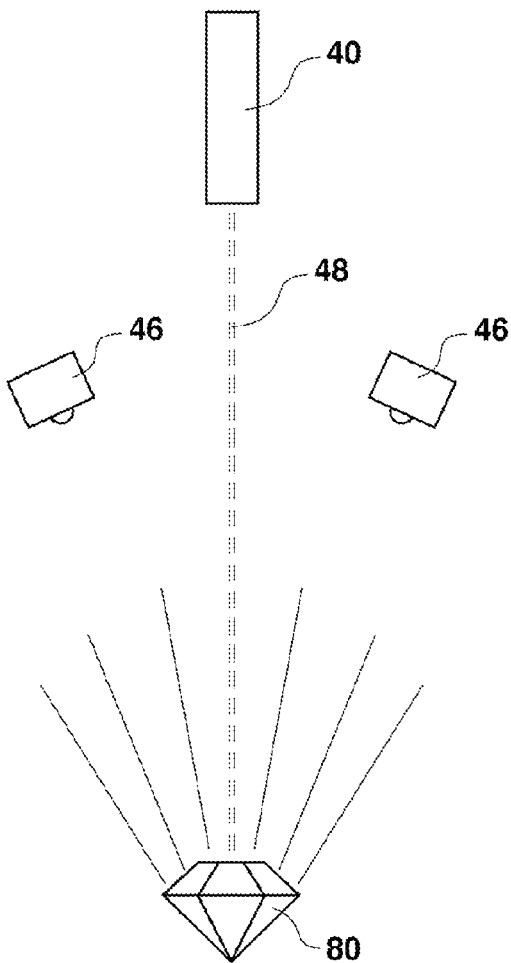
FIG. 1. Theoretical Principles of the Utility Gem Tester shows the ultra-violet solid state laser collimated beam illuminating a gemstone which emits broad spectral luminescence to an array of solid state detectors capable of electronically responding to the spectral content from visible to infrared.

FIG. 1, Theoretical Principles of the Utility Gem Tester, illustrate the fundamental theory and simple geometry of illuminating a 80 GEMSTONE with a 48 LASER BEAM from a 40 UV LASER DIODE ASSEMBLY in order that a 46 SOLID STATE PHOTO DETECTOR ARRAY receive the fluorescence of the 80 GEMSTONE. This illustration assumes a darkened environment and highly collimated 48 LASER BEAM. In the best mode of practice of the invention, the 80 GEMSTONE and SOLID STATE PHOTO DETECTOR ARRAY are miniaturized solid state commercially available assemblies that comply with the general specifications shown in Table 1. Extensive testing of a variety of gemstones have confirmed that the responsive signal output of the SOLID STATE PHOTO DETECTOR ARRAY results in a unique categorized tabulation of digital outputs that dependably and accurately identifies the gemstone with much more accuracy than the human eye can discern. Heretofore, achieving a functioning system utilizing the applicable theory, as discussed in the prior sections, required expensive, complex and space consuming equipment which was best managed by specially trained people. The following drawings will show that the theory of operation can now be achieved in a compact, hand-held and low cost Utility Gem Tester.

FIG. 2, Utility Gem Tester, shows the component assembly of 30 TESTING PROBE, 50 TESTING STAND and 32 GEM RECEPTACLE. In general use of the Utility Gem Tester, a 80 GEMSTONE is inserted into the 32 GEM RECEPTACLE which is then inserted into the 50 TESTING STAND directly below and on center of the 54 PROBE WELL. The user then inquires of the Utility Gem Tester by entering a sequence of programmed instructions from the 60 TEST BUTTON ARRAY.

The user then inserts the 30 TESTING PROBE into the 54 PROBE WELL and depresses the 38 PROBE TEST BUTTON. Within a short interval, the user will get a response to his 60 TEST BUTTON ARRAY input inquiry which will confirm the type and quality of the 80 GEMSTONE.

There are other modes of operation. The illustrated 32 GEM RECEPTACLE is a generic one for either a gemstone or a ring which may be inserted into a diametric slot in the 32 GEM RECEPTACLE. It is also possible to machine other receptacles that will hold other gems of various sizes and shapes. In the alternative, the 30 TESTING PROBE may be handheld and pressed directly against a gem, totally bypassing the step of inserting the probe into the 54 PROBE WELL. As discussed in the prior section, there is a programmed electronic protocol that pretests for ambient light which is accounted for in determining the fluorescence of the gem. This Utility Gem Tester may be handheld and is totally portable and self powered. It may be confidently carried in the field by amateurs when the open cavity of the 54 PROBE WELL is sealed with the 52 PROTECTIVE CAP.

FIG. 3, Utility Gem Tester Assembly, shows the 10 TEST ASSEMBLY of the 30 TESTING PROBE inserted into the 54 PROBE WELL of the 50 TESTING STAND with the 32 GEM RECEPTACLE in place inside the test chamber under the probe. FIG. 3 is intended to show the internal components of the 50 TESTING STAND when the 10 TEST ASSEMBLY is ready to execute a 80 GEMSTONE inquiry from the 60 TEST BUTTON ARRAY.

The 10 TEST ASSEMBLY is a handheld, portable instrument with its contained 62 BATTERIES and logic processing 64 ROM TESTING CIRCUIT BOARD with its MCU which contains the heuristic tabulation of the solid state photo detector array and gemstone identity and quality. The user interface comprises the 60 TEST BUTTON ARRAY setting the operation mode and accepting the inquiry of the user and then the 58 ALPHA-NUMERIC READOUT presents the Utility Gem Tester's response in respect to the type and quality of the 80 GEMSTONE. The 80 GEMSTONE mounted on the 32 GEM RECEPTACLE has been restricted to alignment with the UV laser beam from the 30 TESTING PROBE by the 74 RECEPTACLE RETAINER. Access to the gem testing chamber is accomplished by opening the 56 FLIP LID which is secured to the 50 TESTING STAND by the 66 PIVOT PIN. Easy access to the 62 BATTERIES is routinely accomplished by opening the usual snap locking 68 BATTERY COVER.

The general programmed inquiries which are of primary interest to the amateur user are the initial guess of the user as to check if the 80 GEMSTONE is Ruby, Sapphire, Spinal, Alexandrite, Emerald or Garnet. There are additional inquiries about the fluorescence being red, green, blue, or variable.

Permutations and combination depressions of multiple keys on the 60 TEST BUTTON ARRAY can also give other MCU inquiries to the electronic tabulation on the ROM TESTING CIRCUIT BOARD.

The general output information on the 58 ALPHA-NUMERIC READOUT is the gemstone name accompanied with 'GENUINE', 'CULTURED', or 'IMITATION'. Possible other test outcomes include 'TRY AGAIN' and 'NO SENSOR' to cover possible testing blunders or uniqueness. The inventors have ongoing research for more sophisticated models of the Utility Gem Tester that will be capable of displaying more detailed information on the quality of the gemstone being tested.

FIG. 4, Probe Cross Section, shows the internal compact and simple layout of the 30 TESTING PROBE. The 70 PROBE CABLE supplies the power input and communicates the electrical information of the spectral fluorescence to the 50 TESTING STAND. As previously stated, this 30 TESTING PROBE can be used as a hand-held instrument without physically mating to the 50 TESTING STAND. The lead into the probe is accomplished by a 34 CABLE CONNECTOR which mates with the individual wires of the 70 PROBE CABLE to the 36 PROBE CIRCUIT BOARD which distributes the incoming and outgoing signals to and from their respective source and sink. The testing sequence is initiated by depressing the 38 PROBE TEST BUTTON. In the lower section of the 30 TESTING PROBE are the commercially available 40 UV LASER DIODE ASSEMBLY and the 46 SOLID STATE PHOTO DETECTOR ARRAY with its supplied electronic components. Table 1 gives typical specifications for these commercially available solid state electro-optical devices. The small hole in the center of the 42 PHOTO DETECTOR ARRAY MOUNTING BOARD acts as an ancillary 44 LASER BEAM COLLIMATOR that permits the transmission of the 48 LASER BEAM to exit the probe. The 42 PHOTO DETECTOR ARRAY MOUNTING BOARD holds the necessary logic hardware to process the photodiode information as well as serving as a mounting base for the 46 SOLID STATE PHOTO DETECTOR ARRAY. The production probe has pen/pencil dimensions and is comfortably finger held.

Summary Remarks on the Invention and Operation of the Utility Gem Tester

Not illustrated, but currently under development and in the prototype stage, is an integral Utility Gemstone Tester of slightly modified and obvious architecture which still conforms to the necessary criteria of being a UTILITY ELECTRONIC PRECIOUS GEMSTONE TYPE AND QUALITY DETECTOR which is handheld and simple to operate in the field. This prototyped integral Utility Gemstone Tester contains the functioning components of the TESTING PROBE and the TESTING STAND sans PROBE CABLE in a single compartmentalized architectural shell.

The within invention is not intended to be limited to any narrow interpretation of the description herein. For example, the batteries can either be the classical single use kind or a rechargeable and its recharger component. The ROM component device is of the broad category which includes a PROM section to accept real time data outputs of the active components. The process algorithms implied in the above device description are well established public domain programs which convert analog to digital and perform various mathematical manipulations of such digital data on commercialized chips. There is also another obvious minor modification of the proposed system that employs a WLAN chip to make the described device compatible with the popular WIFI™ and its applications software. This radio transmission modification gives more versatility to the tabulation index of the ROM or even substitutes for the ROM, but requires the use of the ancillary personal computers, video-game consoles, smartphones, some digital cameras, tablet computers or digital audio player to be within 20 meters. The dynamics of communication technology makes simple and obvious updating of the described model device quite amenable to modification inclusive of the within general description.

Lapidaries have been evaluating precious gemstones from time immemorial. The purchaser or finder of a potential precious gemstone has been dependent on the opinion of such lapidary experts. Moreover, the determination of value and quality has often been a subject of dispute. Over time, technology and science have derived techniques and instrumentation to take the guesswork out of evaluating gemstones. But, for the most part, the necessary equipment has been costly, bulky and complex. It was the objective of the invention to fill a long felt need for a low cost, simple and compact device for use by the general public. This objective has been met as a consequence of relatively recent developments in small, efficient and low cost solid state electro-optical devices and an extensive R&D program by the inventors. The prior system drawings well illustrate that this objective has been successfully met as a consequence of several years of laboratory research by the inventors.

TABLE 1

OF COMMERCIALLY AVAILABLE PHOTOACTIVE COMPONENTS

Generic UV LASER DIODE ASSEMBLY
OPELUS TECHNOLOGY CORPORATION

| | |
|---|---|
| part number | E80-405-01-06 |
| output mode | CW |
| wavelength | 405 nm |
| optical power | 1 mw-max |
| Spot shape | dot |
| beam divergence | 5 mrad-max |
| operating voltage | 6.0 voltsDC |
| operating current | 60 ma-max |
| operating temperature | "−10° to +70° C." |
| lifetime | 10,000 hrs |

Generic SOLID STATE PHOTO DETECTOR ARRAY
TAOS, Inc // ams AG

| | |
|---|---|
| part number | TCS 3404 & 3414 |
| operating voltage | 2.7 TO 4.6 voltsDC |
| operating temperature | "−30° to +70° C. |
| number of photodiodes | 16 |
| digital output accuracy | 16 bits |
| specification reference | TCS-3404_TCS3414A.pdf |
| internet site | www.ams.com/eng |

The inventors herein claim:

1. A utility electronic precious gemstone type and quality detector employing ultraviolet laser induced fluorescence in a gemstone of a test assembly of
   a testing stand,
   a testing probe and
   a gem receptacle for holding a gemstone comprising on said testing stand,
   a probe well located on a flip lid connected to said testing stand by a pivot pin and a test button array of depressible buttons to input inquiries concerning said gemstone and an alpha-numeric readout for visually displaying a response to input inquiries based on fluorescence characteristics of said gemstone and in said testing stand,
   a ROM testing circuit board with a micro controller unit that indexes encoded heuristic data tabulation of gemstone identity and quality to digital spectral information in response to inquiry from said test button array as output to said alpha-numeric readout and a gem receptacle retainer for holding said gem receptacle on-center below said probe well and batteries for powering said test assembly where said batteries are accessible by a latching battery cover and a probe cable containing wires from within said testing stand that mates said batteries, said test button array, said ROM testing circuit board and said alpha-numeric readout to said testing probe which contains components of a cable connector that fans out the wires from within said probe cable into a probe circuit board which electrically connects to a UV laser diode assembly and a solid state photo detector array mounted on a photo detector array mounting board that has a laser beam collimator aperture and also holds the matrix of said solid state photo detectors and on the exterior of said testing probe is a probe test button which, on depressing, initiates a sequence of electronic signals on said probe circuit board;

wherein inserting said gemstone into said gem receptacle and placing said gem receptacle into said receptacle retainer within said testing stand, then inserting said testing probe into said probe well and inputting an inquiry by depressing button(s) on said test button array and then depressing said probe test button to initiate a sequence of electronic signals from said probe circuit board that activates said solid state photo detector array to obtain an ambient light spectrum data and then initiates said UV laser diode assembly to emit a laser beam through a laser beam collimator which illuminates said gemstone which fluoresces a spectrum to said solid state photo detector array where each spectrally limited photo-detector luminescence output channel is digitally encoded on said photo detector array mounting board for transmitting its digital information to said ROM testing circuit board which processes and decodes the digital inputs to the tabulation of gemstones digital information to evaluate type and quality of said gemstone which is displayed on said alpha-numeric readout.

2. The test assembly as described in claim 1 further comprising a dimensional architecture that is hand held.

3. The test assembly as described in claim 1 further comprising
a testing probe which may be placed directly against a gemstone for evaluating said gemstone.

4. The test testing probe as described in claim 1 further comprising commercially available UV laser diode assembly which operates in the 400 nanometer UV optical spectral range and outputs less than 1 milliwatt of spectral power.

5. The test testing probe as described in claim 1 further comprising commercially available solid state photo detector array with its associated photo detector array mounting board of a matrix of multiple filtered photo detectors that has a composite spectral range from the visible to the infra-red in multiple spectral channels with a luminosity sensitivity of up to 16 bits output in each spectral channel.

6. The test testing probe as described in claim 1 further comprising
a dimensional architecture similar to a scribing pen so that said testing probe is finger held.

7. The probe circuit board as described in claim 1 further comprising a wireless local area network (WLAN) chip that links to a local transmitter/receiver for wireless operation.

8. The gem receptacle as described in claim 1 further comprising diametrically positioned slots for retaining various jewelry pieces holding gemstones in alignment with said laser beam.

9. An integral utility electronic precious gemstone type and quality detector employing ultraviolet laser induced fluorescence in a gemstone of (a) an integral utility gem tester device of components contained in a single dual sectionalized shell comprising on the exterior shell surface of said integral utility gem tester device is a gem receptacle cavity for retaining a gemstone a test button array of depressible buttons to input inquiries about said gemstone an alpha-numeric readout for visually annunciating the responses to input inquiries, a probe test button for initiating a sequence of signals for performing an identification and quality evaluation of said gemstone, and within the first shell section of said integral utility gem tester device is batteries for supplying power to said device components and said batteries are accessible through a latching battery cover and a probe circuit board for controlling a sequence of initiating signals from and to the various electronic components through connecting electrical conduits and a ROM testing circuit board with a micro controller unit which processes the digital signals from the various electronic components for indexing to a heuristic tabulation that relates processed input digital data from components of said integral utility gem tester device to output information of gemstone identity and quality on said alpha-numeric readout and within the second shell section are commercially available solid state photoactive components of a UV laser diode assembly that optically outputs a UV laser beam through a laser beam collimator aperture in a photo detector array mounting board that holds its matrix of a solid state photo detector array so that said laser beam illuminates said gemstone and causes it to fluoresce;

wherein inserting said gemstone into said a gem receptacle cavity and depressing a sequence of buttons on said test button array to establish an inquiry about said gemstone and then depressing said probe test button to imitate a pretest signal from said probe circuit board to obtain ambient light digital output from said solid state photo detector array for retention in said ROM testing circuit board and then said probe circuit board initiates a signal to said UV laser diode assembly to initiate said laser beam to illuminate said gemstone and cause it to fluoresce so that said solid state photo detector array and its associated said photo detector array mounting board then spectrally analyze the fluorescence into multichannel digital input to said ROM testing circuit board which processes digital information in memory to index to its heuristic tabulation for relating the input information to identify and quality of said gemstone in response to input inquiry and display gemstone identity and quality on said alpha-numeric readout.

10. The integral utility gem tester device shell as described in claim 9 further comprising
a dimensional architecture that is hand held.

11. The UV laser diode assembly as described in claim 9 further comprising
a commercially available LED which operates in the 400 nanometer UV optical spectral range and outputs no more than 1 milliwatt of spectral power.

12. A solid state photo detector array with its photo detector array mounting board as described in claim 9 further comprising commercially available solid state photo detector array with its associated photo detector array mounting board of a matrix of multiple filtered photo detectors that has a composite spectral range from the visible to the infra-red in multiple spectral channels with a luminosity sensitivity of up to 16 bits output in each spectral channel.

13. The probe circuit board as described in claim 9 further comprising
a wireless local area network (WLAN) chip that links to a local transmitter/receiver for supplementary gem data.

* * * * *